United States Patent [19]

Moy et al.

[11] 4,096,194

[45] Jun. 20, 1978

[54] HIGH PURITY ISO-BUTYLENE RECOVERY

[75] Inventors: David Moy; Marvin S. Rakow, both of East Brunswick, N.J.

[73] Assignee: Cities Service Company, Tulsa, Okla.

[21] Appl. No.: 710,982

[22] Filed: Aug. 2, 1976

[51] Int. Cl.² .............................................. C07C 29/04
[52] U.S. Cl. .................................. 568/899; 568/896; 568/897; 568/900; 568/901
[58] Field of Search ........................................ 260/641

[56] References Cited

U.S. PATENT DOCUMENTS

| | | | |
|---|---|---|---|
| 2,477,380 | 7/1949 | Kreps et al. | 260/641 |
| 3,257,469 | 6/1966 | Kovach | 260/641 |
| 3,347,939 | 10/1967 | Bonetti et al. | 260/641 |
| 3,801,656 | 4/1974 | Frampton et al. | 260/641 |

*Primary Examiner*—Joseph E. Evans
*Attorney, Agent, or Firm*—George L. Rushton; John W. Carpenter

[57] ABSTRACT

An improved process for hydrating with liquid water over a solid catalyst and with a liquid solvent a liquid iso-olefin selected from the group consisting of $C_4$ iso-olefins and $C_5$ iso-olefins to form a corresponding product alcohol in the liquid state. The improvement comprises maintaining the liquid iso-olefins, the solvent, and the water in a single liquid phase in order to increase the conversion percentage of the iso-olefin to the corresponding alcohol.

5 Claims, No Drawings

4,096,194

HIGH PURITY ISO-BUTYLENE RECOVERY

BACKGROUND OF THE INVENTION

1. Field of the Invention

This invention relates to an improved process for hydrating with liquid water a liquid iso-olefin over a solid catalyst and with a liquid solvent. More particularly, this invention provides for the hydration of isobutylene to teritiary butyl alcohol in the presence of a solid catalyst.

2. Description of the Prior Art

The general technology of hydrating olefins by using a solid catalyst is well known and well summarized in the disclosure of U.S. Pat. No. 3,285,977 (Henke). Broadly, the methods of hydration of olefins with a solid hydration catalyst generally involve the contacting of olefins in either the gaseous phase, or a separate liquid phase, with water in the liquid phase. The method utilizing the gaseous olefin phase is described in Fiat Final Report number 968 by Kammameyer and Carpenter. The gas liquid system results in a conversion of about 30% or less. The Henke patent utilizes the liquid system with 2 separate liquid phases which results in a conversion of the olefin to the corresponding alcohol of less than 60%. The two phase liquid system was utilized to eliminate difficulties in separation of the produce alcohol from the combination of water and feedstock. The alcohol could be separated from the water and, separately, the alcohol could be separated from the feedstock. However, this process still encountered the practical problem that some water would dissolve in the olefin feedstock and some olefin would dissolve into the water. This would retard the amount of olefin that could be converted into the corresponding alcohol. Therefore, what is needed and what has been invented by us is an improved process which doesn't include the defiencies associated with the prior art.

SUMMARY OF THE INVENTION

It is therefore an object of this invention to provide an improved, economical process for hydrating with liquid water a liquid iso-olefin over a solid catalyst and with a liquid solvent.

It is another object of this invention to provide an improved, economical process for the hydration of isobutylene to tertiary butyl alcohol in the presence of a solid catalyst.

Still other objects will be apparent to those skilled in the art from the following description of this invention.

The foregoing objects are achieved according to the practice of this invention. Broadly, this invention provides an improved process for hydrating with liquid water over a solid catalyst and with a liquid solvent a liquid iso-olefin selected from the group consisting of $C_4$ iso-olefins and $C_5$ iso-olefins to form a corresponding product alcohol in the liquid state. The improvement comprises maintaining the liquid iso-olefin, the solvent, and the water in a single liquid phase in order to increase the conversion percentage of the iso-olefin to the corresponding alcohol.

Thus, by the practice of this invention there is provided an economical, improved process for preparing the corresponding product alcohol in the liquid state from hydrating with liquid water over a solid catalyst and with a liquid solvent a liquid iso-olefin selected from the group consisting of $C_4$ iso-olefins and $C_5$ iso-olefins.

DETAILED DESCRIPTION OF THE INVENTION

This invention provides an improved process for hydrating with liquid water over a solid catalyst and with a liquid solvent, a liquid iso-olefin selected from the group consisting of $C_4$ iso-olefins and $C_5$ iso-olefins to form a corresponding product alcohol in the liquid state. The improvement comprises maintaining the liquid iso-olefin, the solvent, and the water in a single liquid phase in order to increase the conversion percentage of the iso-olefin to the corresponding alcohol. Preferably, this improvement in the process is conducted at a pressure of between about 300 psia and 3000 psia. More preferably, the pressure is between about 300 psia to 600 psia; most preferably, the pressure is between about 300 psia and 400 psia. The temperature is, preferably, between about 80° and 150° C; most preferably, the temperature is between about 90° and 110° C.

The solid hydration catalyst employed in this invention may be any solid hydration catalyst. Suitable catalysts are sulfonic acid resins, blue oxide of tungsten, tungsten sulfide, nickel sulfide, unsupported nickel-tungsten sulfide, supported sulfided nickel-tungsten sulfide and ion exchange resins such as sulfonated polystyrenedivinylbenzene copolymer. Other solid olefin hydration catalysts are alumina, thoria, zirconia, aluminum sulfate, kaolin, titania, etc.

The liquid solvent utilized in our improved process is preferably selected from the group consisting of glycols, glycol ethers, and glycol diethers. The glycols may be dipropylene glycol or propylene glycol. The glycol ethers may be any one selected from the group consisting of methyl cellosolve, butyl cellosolve, monomethyl ether of diethylene glycol, and the monomethyl ether of propylene glycol. The glycol diethers are preferably either the diethyl or dimethyl ethers of diethylene glycol. In a preferred embodiment of the invention the liquid solvent is preferably monomethyl either of propylene glycol or dimethyl ether of diethylene glycol.

The solvent to water weight ration employed in this invention may be any ratio wherein for any selected solvent, there is sufficient solvent present to give the single liquid phase which increases the conversion precentage. In a preferred embodiment of the invention the solvent to water weight ratio is from about 5 to about 20.

The water to iso-olefin mole ratio is preferably from about 3 to about 30. More preferably this ratio is from about 4 to about 10; most preferably, the water to iso-olefin mole ratio is about 6.

The present invention claims that the limitation on conversion of isobutylene to teritiary butyl alcohol is a limitation caused by the equilibrium concentration of isobutylene in the phase layer immediately adjacent to the solid cataylst and by the equilibrium concentration of the tertiary butyl alcohol in the same phase layer. Prior art allowed the water reactant to form a separate narrow layer adjacent to the solid catalyst and a feedstock layer outside of the water layer. The isobutylene had to diffuse through the water phase to reach the reaction site on the solid catalyst. Therefore the concentration of isobutylene was the lowest nearest the catalyst, causing the forward driving force of the hydration reaction to be correspondingly small.

Further, the product, tertiary butyl alcohol was produced on the surface of the solid catalyst and distributed mainly in the water phase, rather than in the isobutylene/olefin feedstock phase layer. Therefore, the water layer adjacent to the solid catalyst increased in concentration of tertiary butyl alcohol as the teritiary butyl alcohol was produced, causing the reverse driving force of the hydration reaction to be increased. The reverse reaction, that is the dissociation of tertiary butyl alcohol, resulted.

With the present invention, the water liquid, solvent, and feedstock form a single phase, thereby eliminating the initial problems of the reactant isobutylene's transport to the site of the reaction.

Also the water -feedstock - liquid solvent solution represents a relatively large homogeneous solution into which the product, tertiary butyl alcohol, readily dissolves, eliminating the tertiary butyl alcohol buildup at or near the reaction site and minimizing the resulting dissociation of tertiary butyl alcohol.

In the following is det forth examples of our invention which are given by way of illustrations and not by limitations. The specific concentrations, temperatures, times, compounds, etc., set forth in these examples are not to be construed to unduly limit the scope of the invention.

EXAMPLE I

Table I shows the results of solvent comparison tests for two liquid phases under the following conditions: Temperature = 200° F, Pressure = 600 psia, Feed = B—B from a Cat Cracker having $iC_4$ of 8.7% wt, B—B LHVSV (Liquid Hourly Volume Space Velocity) = 2, Catalyst = sulphonic acid resin.

Table I

| Solvent | Solvent $H_2O$ Wt Ratio | $H_2O/iC_4$ moles | Conversion of $iC_4$ to Tertiary Butyl Alcohol |
|---|---|---|---|
| Methyl Cellosolve | 4 | 6 | 58% |
| Methyl Cellosolve | 4 | 6 | 61% |
| Methyl Cellosolve | 4 | 12.2 | 68% |
| Methyl Cellosolve | 4 | 11.5 | 64% |
| Methyl Cellosolve | 1 | 7.2 | 46 |
| Methyl Cellosolve | 1 | 17.8 | 50 |
| Methyl Cellosolve | 1 | 11.8 | 40 |
| Butyl Cellosolve | 4 | 6.3 | 64 |
| Dipropylene Glycol | 4 | 6.8 | 65 |
| Dipropylene Glycol | 4 | 12.4 | 69 |
| Dipropylene Glycol | 4 | 6.6 | 62 |
| Dipropylene Glycol | 4 | 6.4 | 60 |
| Propylene Glycol | 4 | 6.5 | 50 |
| Mono-methyl ether of Diethyl Glycol | 4 | 6.8 | 58 |

Table II illustrates the results of a solvent comparison tests for single liquid phase under the same conditions which produced the results of Table I. The results in Table II show the importance of having a solvent to $H_2O$ wt. ratio of at least 5 (depending on the type of solvent employed) in order to obtain a 80% or more conversion of $iC_4$ to tertiary butyl alcohol.

Table II

| Solvent | Solvent/$H_2O$ Wt. Ratio | $H_2O/iC_4$ moles | Conversion of $iC_4$ to Tertiary Butyl Alcohol |
|---|---|---|---|
| Butyl Cellosolve | 15 | 6.3 | 82 |
| Butyl Cellosolve | 15 | 4.5 | 85 |
| Butyl Cellosolve | 15 | 4.1 | 84 |
| Butyl Cellosolve | 10 | 6.6 | 84 |
| Butyl Cellosolve | 10 | 6.2 | 85 |
| Dipropylene Glycol | 15 | 6.1 | 81 |
| Dipropylene Glycol | 15 | 6.1 | 80 |
| Dipropylene Glycol | 15 | 6.2 | 82 |
| Methyl Ether of Propylene Glycol | 10 | 6.3 | 85 |
| Methyl Ether of Propylene Glycol | 6 | 8.4 | 87 |
| Methyl Ether of Propylene Glycol | 6 | 6.6 | 82 |
| Methyl Ether of Propylene Glycol | 6 | 6.4 | 82 |
| Dimethyl Ether of Diethylene Glycol | 10 | 7.1 | 80 |
| Dimethyl Ether of Diethylene Glycol | 9 | 6.6 | 85 |
| Dimethyl Ether of Dietheylene Glycol | 8 | 6.7 | 81 |

EXAMPLE II

Repeat EXAMPLE I but vary the pressure in increments of 25 psia between 300 psia and 3000 psia and the temperature in increments of 5° C between 80° C and 150° C and find similar results.

EXAMPLE III

Repeat Table II in EXAMPLE II but vary the solvent to water weight ratio in increments of 1 from 5 to 20 and find similar results that, depending on the selected solvent, there has to be at least a solvent to water ratio of 5 in order to give the single liquid phase which increases the conversion percentage.

EXAMPLE IV

Repeat EXAMPLE III but vary the water to the iso-olefin mole ratio in increments of 3 between 3 and 30 and find similar results.

EXAMPLE V

Repeat EXAMPLE IV but vary the catalyst from the sulfonic acid resin to one selected from the group consisting of blue oxide of tungsten, tungsten sulfide, nickel sulfide, unsupported nickel-tungsten sulfide, supported sulfided nickel-tungsten sulfide, ion exchange resins such as sulfonated polystyrene-divinylbenzene copolymer, aluminia, thoria, zirconia, aluminum sulfate, kaolin, and titania, and find similar results.

EXAMPLE VI

Repeat EXAMPLE V but vary the solvent from the particular solvent stated to one selected from the group stated in the foregoing specification and find similar results.

EXAMPLE VII

Repeat EXAMPLE VI but change $iC_4$ to $iC_5$ and find similar results.

While the present invention has been described herein with reference to particular embodiments thereof, and specific examples, a latitude of modifications, various changes and substitutions are intended in the foregoing disclosure, and in some instances some features of the invention will be employed without a corresponding use of other features without departing from the scope of the invention as set forth.

We claim:

1. An improved process for hydrating, with liquid water over a solid catalyst and with a liquid solvent, isobutylene to form tertiary butyl alcohol in the liquid state, wherein the improvement comprises using a solvent selected from the group consisting of glycols, glycol ethers, and glycol diethers, and maintaining a solvent-to-water weight ratio of from about 5:1 to about 20:1, thus maintaining a single liquid phase for the reaction mixture and increasing the conversion percentage of the isobutylene to the corresponding alcohol.

2. The process of claim 1 wherein said maintaining step is conducted at a pressure of between about 300 psia and 3000 psia and at a temperature of between about 80° C and 150° C.

3. The process of claim (4) 2, wherein
said lycols are selected from the group consisting of dipropylene glycol and propylene glycol,
said glycol ethers are selected from the group consisting of methyl cellosolve, butyl cellosolve, monomethyl ether of diethylene glycol, and monomethyl ether of propylene glycol, and
said glycol diethers are selected from the group consisting of the diethyl and dimethyl ethers of diethylene glycol.

4. The process of claim 1 wherein said solid catalyst is a sulfonic acid resin.

5. The process of claim 1 wherein said water and said iso-olefin have water to iso-olefin mole ratio of from about 3 to about 30.

* * * * *